United States Patent
Kling et al.

[11] Patent Number: 6,019,963
[45] Date of Patent: Feb. 1, 2000

[54] DEODORIZING COMPOSITION CONTAINING TEA TREE AND EUCALYPTUS OILS

[75] Inventors: Kimberly Mark Kling; Edward Albert Kling, both of Norton Shores, Mich.

[73] Assignee: D.S.C. Products, Inc., Muskegon, Mich.

[21] Appl. No.: 09/197,051

[22] Filed: Nov. 20, 1998

[51] Int. Cl.$^7$ .................. A61L 9/00; A61L 9/04; A61L 11/00; A61L 9/01; C11B 9/00

[52] U.S. Cl. .................. 424/76.1; 424/76.4; 424/76.5; 424/76.6; 424/76.9; 512/5

[58] Field of Search .................. 424/76.1, 76.4, 424/76.5, 76.6, 76.9; 512/5

[56] References Cited

FOREIGN PATENT DOCUMENTS

| 96/25373 | 8/1996 | WIPO . |
| 96/28032 | 9/1996 | WIPO . |
| 96/28033 | 9/1996 | WIPO . |

*Primary Examiner*—Shelley A. Dodson
*Assistant Examiner*—Marina Lamm
*Attorney, Agent, or Firm*—Warner Norcross & Judd LLP

[57] ABSTRACT

A deodorizing dispersion effective for reducing the odor intensity of an odorous material, the dispersion including effective amounts of tea tree oil and eucalyptus oil, preferably dispersed in an aqueous carrier phase. The dispersion optionally includes dispersing agents, such as thickeners, surfactants, and solvents, to promote the stability and uniformity of the dispersion and provide cleaning and detergency attributes.

17 Claims, No Drawings

6,019,963

DEODORIZING COMPOSITION CONTAINING TEA TREE AND EUCALYPTUS OILS

BACKGROUND OF THE INVENTION

The present invention relates to deodorizing dispersions, and more particularly, to deodorizing dispersions incorporating tea tree and eucalyptus oils.

Materials can take on an offensive odor under several circumstances. For example, a carpet that has been exposed to water from storm, flood, overflow, or pipe breakage will smell of the mold and mildew that subsequently form in the carpet. Also, a fabric or carpet can smell of urine and feces deposited by a pest or household pet. The growth of microorganisms associated with such deposits or floods can contribute significantly to the foul smell. Further, entire contents of fire-damaged buildings may retain the strong smell of smoke.

Deodorizing compositions are available to disinfect, remove, or mask these offensive odors in order to salvage or restore the exposed materials. U.S. Pat. No. 5,610,189 to Whiteley issued Mar. 11, 1997 entitled "Disinfecting Composition" discloses a disinfecting and deodorizing composition containing tea tree oil. Tea tree oil is distilled or extracted from the leaves of the tea tree (*Melaleuca alternifolia*), which is native to Australia. Tea tree oil has natural antiseptic, germicide, fungicide, and cleaning attributes, and a characteristic odor, for which Whiteley recommends added perfume or odor maskant for cosmetic appeal. (Col. 6, lns. 9–16.)

Neuman Industries, Inc. supplies a deodorizing composition under the NC 2000 trademark. The NC 2000 contains an unspecified amount of eucalyptus oil; the other components are not disclosed. The NC 2000 product has been applied as a fine mist in the air to deodorize pig farms.

Felton Grimwade & Bickford Pty. Ltd. of Oakleigh South, Victoria, Australia supply two cleaner/deodorizer products under the BOSITO'S PARROT BRAND trademark: the first containing 25% eucalyptus oil in a hydrocarbon propellant, the second containing 100% eucalyptus oil.

Although these compositions can be used to treat odorous materials, the need still exists for effective deodorizing formulations.

SUMMARY OF THE INVENTION

The aforementioned problems are overcome in the present invention wherein a deodorizing dispersion useful for reducing the odor intensity of an odorous material includes effective amounts of tea tree oil and eucalyptus oil. The tea tree and eucalyptus oils can be dispersed in a carrier phase, such as an aqueous carrier phase. The deodorizing dispersion optionally includes effective amounts of one or more dispersing agents, such as a thickening agent, a surfactant, and a solvent.

The present invention also includes a method of reducing the intensity of an odor by applying an effective amount of a deodorizing dispersion, which contains effective amounts of tea tree oil and eucalyptus oil.

In one embodiment of the present invention, the active deodorizing components of the dispersion are essentially the tea tree and eucalyptus oils. In another embodiment of the present invention, the dispersing agents are essentially biodegradable.

The deodorizing dispersion of the present invention combines effective amounts of the natural essential oils of the tea tree and eucalyptus tree to form an effective composition for treating odorous materials. The deodorizing dispersion can be used with conventional application methods and equipment. Further, the deodorizing dispersion can be formulated essentially with only natural or biodegradable components. The deodorizing dispersion does not require synthetic or masking perfume to counter the otherwise noticeable and characteristic smell of tea tree oil. Also, the deodorizing dispersion does not weaken the stain-resistant treatment (e.g., the fluorocarbon-based protectant) of treated fabrics.

These and other objects, advantages, and features of the invention will be more readily understood and appreciated by reference to the detailed description of the preferred embodiments.

DETAILED DISCUSSION OF THE PREFERRED EMBODIMENTS

The deodorizing dispersion of the present invention includes effective amounts of tea tree oil and eucalyptus oil. Preferably, these oils are dispersed in a carrier phase, for example, an aqueous continuous phase, which optionally includes a thickener. The dispersion may also include other dispersing agents, such as surfactants and solvents, to promote the stability and uniformity of the dispersion and provide cleaning and detergency attributes.

Tea Tree and Eucalyptus Oils

The deodorizing dispersion includes effective amounts of tea tree and eucalyptus oils. As used herein, "effective amounts" includes amounts that upon application to an odorous material act to reduce the odor intensity. Odorous materials include hard surfaces (e.g., floors, walls, plaster) or porous materials (e.g., carpets, upholstery, drapes, clothing, mattresses, insulation) that have been soiled or damaged by mold, mildew, microorganisms, urine, feces, sewage, or smoke. In addition to providing deodorizing attributes to supplement those of tea tree oil, eucalyptus oil also counteracts or reduces the naturally unpleasant, characteristic smell of the tea tree oil in the dispersion, so that consumers will not be offended by the aroma of the tea tree oil in the dispersion. Both tea tree oil and eucalyptus oil are considered "natural" components—that is, components found in or produced by living things. Accordingly, both of these oils are natural, odor-reducing or deodorizing active components.

Effective amounts of tea tree oil and eucalyptus oil include a relative weight ratio of tea tree oil to eucalyptus oil ranging from about 100:1 to about 1:100, preferably from about 10:1 to about 1:10, more preferably from about 2:1 to about 1:2, most preferably about 1:1. The dispersion may be essentially free of components other than tea tree and eucalyptus oils. However, since these oils are relatively expensive, it is preferable to disperse these components in a carrier phase to achieve cost efficient coverage and contact of the oils with an odorous material.

As discussed below, the deodorizing dispersion can be provided in relatively concentrated form for shipment or in relatively diluted form for application. Preferred concentrations depend on the deodorizing application. Generally, deodorizing applications fall into one of four categories of increasing deodorization difficulty:

| Class | Application |
|---|---|
| I | Portable Extractors and Ready-To-Use Sprays |
| II | Hard Surfaces; General Deodorization; Laundry |
| III | Restoration of Materials Exposed to Clean Water; Carpet Prespray; Truckmount Additive |
| IV | Restoration of Materials Exposed to Sewage Back-up, Urine, Unsanitary Water, Putrefied Items; Water & Fire Restoration |

Effective amounts for each of the tea tree and eucalyptus oils in diluted form can depend on the class of application, and include the amounts shown in the table below:

| Class/Application | Wt % Range | Preferred Wt % | More Preferred Wt % |
|---|---|---|---|
| Concentrate | 0.1 to 15 | 0.5 to 5 | 1 |
| Class I | 0.0005 to 0.04 | 0.005 to 0.03 | 0.02 |
| Class II | 0.003 to 0.08 | 0.01 to 0.06 | 0.05 |
| Class III | 0.08 to 0.25 | 0.10 to 0.20 | 0.15 |
| Class IV | 0.25 to 2 | 0.4 to 1.0 | 0.5 |

"Tea tree oil" as used herein includes the extract from the tea tree (*Melaleuca alternifolia*), preferably the leaves. Tea tree oil is described in U.S. Pat. No. 5,610,189 to Whiteley issued Mar. 11, 1997 entitled "Disinfecting Composition," which is incorporated in its entirety by reference. Tea tree oil contains almost 50 compounds, including monoterpenes, sequiterpines, and terpene alcohols. The Australian standard for tea tree oil requires that the oil contain at least 30 weight percent terpinen 4-ol and not more than 15 weight percent cineole.

"Eucalyptus oil" as used herein includes the extract from a species of eucalyptus tree (genus Eucalyptus), preferably the leaves. Eucalyptus species include *piperita, radiata, globulus, oleaosa, cneorifolia, citriodora, polybractea, australiana*, and *dives*; preferably one of the latter three species. Eucalyptus oil contains varying amounts of cineole, terpineol, citral, citronellal, phellandrene. Pharmaceutical quality eucalyptus oil contains at least 70% cineole.

Extraction methods for obtaining tea tree or eucalyptus oil are known in the art, and include pressing, steam distillation, or extraction with a solvent.

Carrier Phase

The effective amounts of tea tree and eucalyptus oils are preferably dispersed in a carrier phase. As used herein, a "dispersion" means a stable, uniformly dispersed mixture, and includes a blend, mixture, colloidal solution, true solution, suspension, and emulsion. The carrier phase may be aqueous or hydrocarbon based. If aqueous based, suitable organic solvents include alcohols, ketones, chlorinated solvents, and esters. If hydrocarbon based, preferably the hydrocarbon carrier is essentially volatile, so that the carrier will evaporate after application. Suitable hydrocarbon based carriers include aliphatic, aromatic, and terpene hydrocarbons. If aqueous based, the aqueous carrier is essentially continuous in the dispersion. The primary component of the aqueous phase is water. Water is preferred because it is an inexpensive, nontoxic carrier.

In order to decrease the weight of the deodorizing dispersion, and thus save cost during shipment, the dispersion can be formulated to be shipped in a relatively concentrated form with respect to non-carrier components. Before application of the dispersion to an odorous material, the end-user can dilute the dispersion with the carrier (e.g., water) to form the desired deodorizing dispersion concentration.

The deodorizing dispersion optionally includes one or more dispersing agents to assist in maintaining the stability or uniformity of the dispersion. The dispersing agents may also provide other desirable attributes to the dispersion. A "dispersing agent" includes surfactants, emulsifiers, thickening agents, hydrotropes, solvents, and mixtures thereof. Preferably, each dispersing agent is biodegradable. As used herein, "biodegradable" means chemically broken down by microorganisms and/or natural environmental factors within an acceptable time given the toxicity of the subject material.

Thickening Agent

A first optional dispersing agent for an aqueous carrier is an effective amount of one or more thickening agents—that is, an amount of hydrophilic substance that increases the viscosity of the deodorizing dispersion to aid in maintaining stability. Generally, "thickening agents" include: (1) starches, gums, casein, gelatin, and phycocolloids, (2) cellulose derivatives, (3) polyvinyl alcohol and carboxyvinylates, and (4) bentonite, silicates, and colloidal silica.

Preferred thickening agents for use with an aqueous carrier include modified celluloses, such as hydroxyethylcellulose, hydroxymethylcellulose, hydroxypropylcellulose, carboxymethylcellulose, and hydroxybutylcellulose, such as the products sold under the trade name CELLOSIZE (QP and WP) by Union Carbide Corporation, NATROSOL (150, 250) by Hercules Corporation, and NATROSOL PLUS GRADE 330 CS by Aqualon Corporation.

Thickening agents also include heterobiopolysaccharides, for example, the xanthan gums marketed under the marks KELTROL and KELZAN by the Kelco Corporation, RHODOPOL and RHODIGEL by the Rhone-Poulenc Corporation, and ACTIGUM by the Ceca/Satia Corporation; carob gums; guar gums; and hydroxypropylguar gums. Also included are crosslinked polyacrylic acids such as Carbopols from the Goodrich Company and SYNTHALEN K, L or M from the Sigma Company; glyceryl poly(meth)acrylate polymers sold under the marks HISPAGEL or LUBRAGEL by the Hispano Quimica Corporation or Guardian Corporation, respectively; polyvinylpyrrolidone; polyvinyl alcohol; crosslinked polymers of acrylamide and ammonium acrylate sold under the marks PAS 5161 or BOZEPOL C by Hoechst Corporation; crosslinked polymers of acrylamide and 2-acrylamido-2-methylpropanesulphonic acid, partially or totally neutralized, sold under the name SEPIGEL 305 by the Seppic Corporation; crosslinked polymers of acrylamide and methacryloyloxyethyl-trimethylammonium chloride sold under the mark SALCARE SC92 by the Allied Colloids Corporation; or homopolymers or copolymers derived from acrylic acid such as the product sold under the mark ACRYSOL ICS-1 by the Seppic Corporation; and polyurethane latexes such as that sold under the mark DSX-1514 by the Henkel Corporation.

Effective amounts of thickening agent can depend on the expected class of application, and include the amounts shown in the table below, based on the total weight of dispersion:

| Class/Application | Wt % Range | Preferred Wt % | More Preferred Wt % |
| --- | --- | --- | --- |
| Concentrate | 0.01 to 3 | 0.1 to 2 | 0.2 |
| Class I | 0.0016 to 0.016 | 0.001 to 0.01 | 0.004 |
| Class II | 0.003 to 0.03 | 0.005 to 0.02 | 0.01 |
| Class III | 0.015 to 0.15 | 0.02 to 0.10 | 0.03 |
| Class IV | 0.06 to 0.20 | 0.08 to 0.20 | 0.1 |

Surfactant

A second optional dispersing agent is an effective amount of one or more surfactants to promote the stability or uniformity of the deodorizing dispersion. Preferably, the surfactant has emulsifying attributes to provide a sufficient hydrophilic-lipophilic balance (HLB) to maintain the deodorizing dispersion in a clear appearance. Surfactants include nonionic surfactants, anionic surfactants, amphoteric surfactants, and, less preferably, cationic surfactants, since cationic surfactants can weaken fluorocarbon-based stain resistant treatments.

Suitable nonionic surfactants include one or more ethoxylates, such as the aliphatic alcohol ethoxylates and alkylphenol ethoxylates. As is known in the art, these nonionic compounds are water-soluble surfactants obtained by condensing ethylene oxide groups with an aliphatic alcohol or alkylphenol. Suitable nonionic ethoxylates include those having either the formula $R_1(OC_2H_4)_nOH$, where $R_1$ is an alkyl group having from 8 to 18 carbons, and n is from 3 to 15; or the formula $R_2C_6H_4(OC_2H_4)_nOH$ where $R_2$ is an alkyl group having from 7 to 10 carbons, more preferably from 8 to 9 carbons, and n is from 3 to 20, more preferably from 8 to 10. Union Carbide Corporation supplies nonylphenol ethoxylates under the TERGITOL trademark, such as TERGITOL NP-9 (where n equals 9). Other suitable nonionic surfactants include poly(oxypropylene)-poly (oxyethylene), alkylene oxide adducts of polyhydric components, such as ethylene oxide adducts of ethylene diamine sold under the TETRONIC mark, and the ethylene oxide propylene oxide adducts of propylene glycol sold under the PLURONIC mark.

In addition to aiding the stability of the deodorizing dispersion, the surfactant: 1) assists in wetting both the material being treated and the foreign substances present on that material and 2) interacts with the foreign material to help lift and suspend it until extracted, removed, or rinsed from the treated material.

Effective amounts of surfactant can depend on the expected class of application, and include the amounts shown in the table below, based on the total weight of dispersion:

| Class/Application | Wt % Range | Preferred Wt % | More Preferred Wt % |
| --- | --- | --- | --- |
| Concentrate | 1 to 15 | 1 to 7 | 2 |
| Class I | 0.0016 to 0.16 | 0.016 to 0.10 | 0.04 |
| Class II | 0.016 to 0.30 | 0.16 to 0.20 | 0.18 |
| Class III | 0.16 to 0.5 | 0.20 to 0.40 | 0.3 |
| Class IV | 0.20 to 5 | 0.5 to 2.0 | 1.0 |

Solvent

A third optional dispersing agent is an effective amount of one or more solvents to promote the stability or uniformity of the deodorizing dispersion. Suitable solvents include alcohols, polyols, glycols, ketones, esters, and glycol ether solvents, their acetates, and mixtures thereof.

Preferred glycol ether solvents include the p-series glycol ethers. P-series glycol ethers are organic ether compounds obtained by the synthesis of alcohols and propylene oxide. P-series glycols have a number of favorable attributes: 1) exhibit non-toxic and non-ozone depleting properties, 2) metabolize to propylene glycol—a common food ingredient, 3) possess surfactant qualities to help dissolve oil-soluble components in aqueous environments, 4) reduce the surface tension of water to penetrate into both water-soluble and oil-soluble solids while wetting the substrate to lift soils, 5) provide coupling capabilities to remove oil-soluble and water-soluble soils from the substrate, 6) suspend soils in solution to prevent redeposition onto the cleaned surface, and 7) exhibit low vapor pressures.

P-series glycol ethers that are useful in the present invention include dipropylene glycol monomethyl ether (DPM), propylene glycol monomethyl ether (PM), propylene glycol monobutyl ether, dipropylene glycol dimethyl ether, dipropylene glycol monopropyl ether, dipropylene glycol monobutyl ether, and butylethoxy propylene glycol, and mixtures thereof. The related compounds of glycol ether acetates, for example, propylene glycol monomethyl ether acetate, can also be used. However, glycol ether acetates should be avoided if the deodorizing dispersion will contact rubber, since these compounds can cause rubber degradation and swelling.

Effective amounts of solvent can depend on the expected class of application, and include the amounts shown in the table below, based on the total weight of dispersion:

| Class/Application | Wt % Range | Preferred Wt % | More Preferred Wt % |
|---|---|---|---|
| Concentrate | 1 to 45 | 1 to 25 | 3 |
| Class I | 0.0024 to 0.24 | 0.024 to 0.10 | 0.06 |
| Class II | 0.09 to 0.50 | 0.12 to 0.30 | 0.15 |
| Class III | 0.24 to 0.75 | 0.35 to 0.65 | 0.45 |
| Class IV | 0.75 to 45 | 1.0 to 2.0 | 1.5 |

Manufacturing the Deodorizing Dispersion

The deodorizing dispersion can be manufactured by any of the conventional mixing methods. The skilled artisan will appreciate that the stability of the deodorizing dispersion is affected by many parameters, including: 1) the choice of dispersing agents (e.g., surfactants, solvents, thickeners), 2) the concentration of the various components, 3) process considerations (e.g., the mixing equipment), 4) the sequence in which the ingredients are added, 5) the speed and duration of the process, and 6) temperature changes.

A suitable method of forming the deodorizing dispersion includes placing the carrier component into a vessel having turbine agitation capable of forming a vortex. After forming a vortex in the carrier component, the optional dispersing agents are slowly added into the vortex to thoroughly disperse these components in the mixture. If an aqueous carrier is used, preferably any optional thickener dispersing agent is added before any optional surfactant or solvent dispersing agent is added. Then, the tea tree and eucalyptus oils are added to the resulting mixture while agitating to disperse the oils and form the deodorizing dispersion.

Alternatively, the deodorizing dispersion can be prepared by a conventional process of emulsification utilizing a high shear or high pressure homogenizer, operated to obtain average droplet sizes sufficiently small to form a stable emulsion, as is known in the art.

Using the Deodorizing Dispersion

The deodorizing dispersion may be supplied in a ready-to-use form or in a concentrated form to save in shipping costs. If supplied in a concentrated form, the end-user dilutes and mixes the dispersion with additional carrier (e.g., water) to form the desired concentration before application. Generally, porous fabrics such as carpets require a more concentrated dispersion than hard-surface applications. Also, a more concentrated dispersion is recommended for strongly fouled and odorous materials. Once formed, the deodorizing dispersion of the present invention will remain stable and retain its deodorizing attributes under normal conditions, including temperature changes, for reasonable periods of time, although agitation before use may be needed if the dispersion has been stored for a long time.

An end user can apply the deodorizing dispersion by hand by soaking a cloth or sponge with the dispersion and then wiping the surface to be deodorized. After waiting about 10 minutes, the user then wipes the surface with a clean cloth or sponge to remove the deodorizing dispersion and foreign materials. Alternatively, a user can apply the deodorizing dispersion by sprayer (e.g., pressure, pump-up, or electric types), water-based fogger, or injector. After about 10 minutes residence time, the dispersion and foreign material may be extracted. In laundry applications, the deodorizing dispersion is added directly to the wash water.

The following example is presented for the purpose of further illustrating and explaining the present invention and is not to be taken as limiting in any regard. Unless otherwise indicated, all parts and percentages are by weight.

EXAMPLE 1

A deodorizing dispersion was prepared having the following weight percentages based on the total formulation:

| Component | Weight Percent | 60 gallon batch amounts: |
|---|---|---|
| Water | 93.56 | 56 gallons |
| Tea tree oil (TTO)[1] | 0.84 | 1.9 kg |
| Eucalyptus oil (EO)[2] | 0.84 | 1.9 kg |
| Polyethoxylated nonylphenol nonionic surfactant[3] | 1.70 | 8.5 lbs |
| Dipropylene glycol monomethyl ether (DPM) solvent | 2.86 | 14.3 lbs |
| Hydroxyethylcellulose thickening agent[4] | 0.20 | 1 lb |

[1]Standard Tea Tree Oil, Product No. FPBULKUSQ, Thursday Plantation Laboratories Ltd., Pacific Highway, Ballina NSW 2478 Australia.
[2]EUCALYPTOL eucalyptus oil, Product No. V-1379, Arylessence Corporation, Marietta, Georgia
[3]TERGITOL NP-9 nonionic surfactant, Union Carbide Corporation
[4]CELLOSIZE thickener, Product No. HEC-QP 100M-H, Union Carbide Corporation The deodorizing dispersion was formed by first placing water at a temperature of from about 10° C. to about 30° C. into a suitable vessel having turbine agitation capable of forming a vortex. After forming a vortex in the water, the thickening agent was slowly added into the vortex to reduce the particle size of the thickening agent particles and facilitate hydrolyzing the mixture into a smooth thickened liquid. Next, the solvent and the surfactant were added to the thickened liquid while agitating to disperse these components throughout the thickened liquid. Then, the tea tree and eucalyptus oils were added to the resulting mixture while agitating to disperse the oils and form the deodorizing dispersion. The resulting dispersion was clear and stable.

The resulting deodorizing dispersion is applied directly or mixed with additional water before application to form a diluted concentration. The following table shows suitable dilutions of the Example 1 deodorizing dispersion for various deodorizing applications as previously classified:

| Application | Dilution[1] | Preferred Dilution[2] |
|---|---|---|
| Class I | 1 to 3 ounces | 2% |
| Class II | 4 to 10 ounces | 5% |
| Class III | 10 to 32 ounces | 15% |
| Class IV | 32 to 128 ounces | 50% |

[1]Volume of Example 1 dispersion per gallon of water.
[2]Volume/volume percent of Example 1 dispersion in dilution.

Comparison Test

A carpet that had been uniformly soiled with cat urine was divided into four areas and treated with equal amounts of different dispersions. The first area was sprayed with a diluted deodorizing dispersion of the present invention ("Dispersion A; eight ounces of the deodorizing dispersion of Example 1 diluted with one gallon of water). The second area was sprayed with a dispersion similar to Dispersion A, but with the eucalyptus oil replaced with an equivalent amount of water ("Dispersion B"). The third area was sprayed with a dispersion similar to Dispersion A, but with the tea tree oil replaced with an equivalent amount of water ("Dispersion C"). The fourth area was not sprayed. The results are shown in the table below:

| Treatment | Initial Result | Result After 24 Hours |
|---|---|---|
| Dispersion A (present invention) | Significantly reduced odor; no residual tea tree oil odor | No residual odor; no odor of tea tree oil |
| Dispersion B | Significantly reduced odor, but with heavy tea tree oil scent | Residual odor; lingering odor of tea tree oil |
| Dispersion C | Slightly reduced odor | Residual odor |
| No Treatment | Odor not reduced | Odor not reduced |

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. Except in the claims and the specific examples, or where otherwise expressly indicated, all numerical quantities in this description indicating amounts of material, reaction conditions, use conditions, molecular weights, and/or number of carbon atoms, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated.

The embodiments of the invention in which an exclusive property or privilege is claimed are defined as follows:

1. A deodorizing dispersion comprising in a carrier:
   from about 0.0005% to about 0.08% of a first natural oil selected from the group consisting of eucalyptus oil and tea tree oil; and
   a second natural oil present in a weight ratio of from about 2:1 to about 1:2 relative to the first natural oil, the second natural oil being selected from the group consisting of eucalyptus oil and tea tree oil, wherein the first and second natural oils are different oils.

2. The dispersion of claim 1 wherein the tea tree oil ranges from about 0.0005% to about 0.08% and the eucalyptus oil ranges from about 0.0005% to about 0.08%.

3. The dispersion of claim 1 further comprising an effective amount of at least one dispersing agent, wherein the carrier phase is aqueous.

4. The dispersion of claim 1 wherein the dispersing agent includes a nonionic surfactant.

5. The dispersion of claim 4 wherein the nonionic surfactant is present from about 0.0016% to about 0.5% by weight of the dispersion.

6. The dispersion of claim 3 wherein the dispersing agent includes from about 0.0024 to about 45% by weight of at least one glycol ether.

7. The dispersion of claim 6 wherein the glycol ether is present from about 0.0024% to about 0.75% by weight of the dispersion.

8. A method of reducing the odor intensity of an odorous carpet comprising applying the deodorizing dispersion of claim 1 to the carpet.

9. A deodorizing dispersion comprising in a carrier:
   an effective amount of tea tree oil;
   an effective amount of eucalyptus oil; and
   an effective amount of one or more dispersing agents selected from the group consisting of surfactants, emulsifiers, thickening agents, and hydrotropes; and
   a solvent in an amount of from about 0.0024% to about 0.75% by weight of the dispersion.

10. The dispersion of claim 9 wherein the solvent is a glycol ether solvent.

11. The dispersion of claim 9 wherein the dispersing agent includes a surfactant in an amount of from about 0.0016% to about 0.5% by weight of the dispersion.

12. The dispersion of claim 9 wherein the tea tree oil ranges from about 0.0005% to about 0.08% and the eucalyptus oil ranges from about 0.0005% to about 0.08%.

13. A deodorizing dispersion consisting essentially of:
   a carrier;
   an effective amount of tea tree oil dispersed in the carrier;
   an effective amount of eucalyptus oil dispersed in the carrier; and
   an effective amount of one or more dispersing agents selected from the group consisting of surfactants, emulsifiers, thickening agents, and hydrotropes.

14. The dispersion of claim 13 wherein the surfactant ranges from about 0.0016% to about 0.5% by weight of the dispersion.

15. The dispersion of claim 13 wherein the tea tree oil ranges from about 0.0005% to about 0.08% and the eucalyptus oil ranges from about 0.0005% to about 0.08%.

16. A method of reducing the odor intensity of an odorous carpet comprising applying the deodorizing dispersion of claim 13 to the carpet.

17. The dispersion of claim 13 wherein the carrier is aqueous.

* * * * *

UNITED STATES PATENT AND TRADEMARK OFFICE
CERTIFICATE OF CORRECTION

PATENT NO. : 6,019,963
DATED : Feb. 1, 2000
INVENTOR(S) : Kling et al

It is certified that error appears in the above-indentified patent and that said Letters Patent is hereby corrected as shown below:

```
Column 10, Claim 4, Line 18:
   "1" should be --3--
```

Signed and Sealed this

Seventh Day of November, 2000

Attest:

Q. TODD DICKINSON

*Attesting Officer*  *Director of Patents and Trademarks*